United States Patent
Erbe et al.

(12) 
(10) Patent No.: US 7,045,125 B2
(45) Date of Patent: May 16, 2006

(54) BIOLOGICALLY ACTIVE COMPOSITES AND METHODS FOR THEIR PRODUCTION AND USE

(75) Inventors: Erik M. Erbe, Berwyn, PA (US); Jeffrey G. Marx, Downington, PA (US)

(73) Assignee: Vita Special Purpose Corporation, Wilmington, DE (US)

( * ) Notice: Subject to any disclaimer, the term of this patent is extended or adjusted under 35 U.S.C. 154(b) by 278 days.

(21) Appl. No.: 10/035,797

(22) Filed: Oct. 23, 2001

(65) Prior Publication Data

US 2002/0127720 A1    Sep. 12, 2002

Related U.S. Application Data

(60) Provisional application No. 60/242,906, filed on Oct. 24, 2000.

(51) Int. Cl.
*A01N 63/00*  (2006.01)

(52) U.S. Cl. .................. 424/93.7; 424/489; 623/16
(58) Field of Classification Search ............... 424/93.7, 424/489; 623/16
See application file for complete search history.

(56) References Cited

U.S. PATENT DOCUMENTS

| | | | |
|---|---|---|---|
| 4,065,360 A | 12/1977 | Kreb, III | 195/139 |
| 4,801,263 A | 1/1989 | Clark | 433/90 |
| 5,772,665 A | 6/1998 | Glad et al. | 604/82 |
| 5,824,084 A | 10/1998 | Muschler | 623/16 |
| 5,939,039 A | 8/1999 | Sapieszko et al. | 423/311 |
| 6,049,026 A | 4/2000 | Muschler | 623/16 |
| 6,383,519 B1 * | 5/2002 | Sapieszko et al. | 424/489 |

OTHER PUBLICATIONS

U.S. Appl. No. 09/253,556, filed Feb. 19, 1999, Sapieszko et al.

* cited by examiner

*Primary Examiner*—Leon B. Lankford, Jr.
(74) *Attorney, Agent, or Firm*—Woodcock Washburn LLP

(57) ABSTRACT

Biologically active composites containing calcium phosphate, more specifically beta-tri-calcium phosphate, and methods of preparing the same are disclosed herein. Also disclosed are methods of restoring an osseous void and complimentary kits for the disclosed composites.

8 Claims, 4 Drawing Sheets

BIOLOGICALLY ACTIVE COMPOSITES AND METHODS FOR THEIR PRODUCTION AND USE

CROSS-REFERENCE TO RELATED APPLICATIONS

This application claims benefit of U.S. provisional Application Ser. No. 60/242,906 filed Oct. 24, 2000.

FIELD OF THE INVENTION

This patent application relates to biologically active composites containing calcium phosphate and methods of preparing the same. Also included are methods of restoring an osseous void using the composites of the present invention and to kits for the preparation and delivery of such composites. In accordance with the invention, the composites can be prepared using calcium phosphate in a variety of different forms, including morsels and blocks. The composite mass generally contains osteoconductive properties and may also exhibit osteoinductive and osteogenic potential by nature of the β-TCP materials.

BACKGROUND OF THE INVENTION

When bone integrity is threatened by trauma, infection, congenital malformation, tumor growth or degenerative diseases, a method of regenerating and healing the affected bone is the use of bone grafts. Bone grafts function in a manner similar to cancellous bone—supporting new tissue growth by providing the bone and blood cells with a matrix through which to interweave, as they reconnect the bone fragments.

There are three processes that are characteristic of a successful bone graft.

(1) osteoconduction—the apposition of growing bone to the three-dimensional surface of a suitable scaffold provided by the graft;

(2) osteoinduction—the biologically mediated recruitment and differentiation of cell types essential for bone; and (3) osteogenesis—the process of bone formation through cellular osteoblastic activity and remodeling through osteoclastic activity, which, in turn, is dependent upon the presence of osteoprogenitor stem cells.

Orthopedists in this field currently use a variety of materials when attempting to enhance these three processes. A sampling of these materials include the autograft, cadaveric allograft, xenograft, and several types of graft materials. These materials are considered basic types of bone substitutes that are used alone and sometimes in combination.

Autogenous bone is generally widely used in this field. Autogenous bone grafts, or autografts, have a number of advantages. They are histocompatible, they do not transfer disease and they retain viable cells that contribute to the formation of new bone including osteoblasts. Histocompatibility, for example, allows the cellular reaction that accompanies implantation to proceed without an immunologic rejection of the graft, and the graft generally integrates well into the graft site. Autografts can be prepared from cancellous bone or cortical bone. However, the latter material typically lacks the porosity required for cellular migration and revascularization.

The anterior or posterior aspect of the iliac crest provides a common donor site from which to harvest autograft material. Donor material from the iliac crest provides osteogenic properties in the form of surviving osteogenic precursor cells. The loose trabecular structure of the iliac crest encourages ingrowth of blood vessels that are necessary to support bone growth by helping to reduce ischemic necrosis of cellular elements. The noncollagenous bone matrix proteins of the iliac crest include growth factors and also provide osteoinductive properties. The bone mineral and collagen in the autograft material transplanted from the iliac crest provide a compatible osteoconductive surface.

Unfortunately, the full potential of autografts are not fully realized in practice because graft processing results in the death of much of the cellular elements. Those cells that survive must initially receive their oxygen via diffusion. Thus, considerable anoxic cell death probably occurs before sufficient vascularization has permeated the graft. Revascularization into the internal regions of the autograft is slow and incomplete and can be inhibited by fibrin clotting in the autograft and by the packing procedure used to place the graft into the surgical site. Packing of the autograft into a surgical site can decrease the porosity of the graft, in turn decreasing the potential for revascularization of the innermost areas of the graft. Cell death in the autograft leaves behind only a bone mineral scaffold.

Among several other shortcomings, the harvesting process of autograft is high in cost. Other shortcomings include the limited quantity of bone available for harvest, significant donor-site morbidity (rates as high as 25%), temporary disruption of donor-site bone structure, complications such as infection and pain, increased operative time and significantly increased operative blood loss. Minor complications include superficial infection and seromas, and minor hematomas. More serious complications include herniation of abdominal contents through massive bone graft donor sites, vascular injuries, deep infections at the donor site, neurologic injuries, deep hematoma formation requiring surgical intervention and iliac wing fractures.

Autograft alternatives include allografts, xenografts and synthetic bone grafts. Allografts are bone grafts harvested from a human donor other than the recipient. They are usually cleaned and processed to remove cells and debris to minimize their potential for eliciting an immune response or to carry infectious agents. Such tissue can be preserved by processes that can compromise mechanical properties like freeze-drying or freezing. As a result of this processing, allografts do not contain living cells and are not osteogenic. Although their properties vary with preparation methods, they generally have osteoconductive properties and can exert a somewhat stimulatory (osteoinductive) effect on cell in-migration and differentiation.

Xenografts are harvested from animals. Because of their immunogenicity, xenografts harvested from another species have generally been impractical for clinical use. Removal of proteinaceous and fatty materials during processing, as is done in the preparation of Kiel bone, or Oswestry bone, reduces immunogenicity. However, the processing required to produce this type of graft removes the osteoinductive matrix proteins. To guarantee viral inactivation, not only cells, but all proteins must be removed, thus eliminating both osteogenic and osteoinductive potential.

As a result, alternative bone-grafting strategies have been investigated. The development of composite grafts that combine synthetic cancellous bone void fillers with autogenous bone-forming cells could simplify and improve grafting procedures.

Accordingly, there is a need to provide methods of preparing a biologically active composite material that is osteoconductive, and at least osteoinductive or osteogenic.

There is a need to provide biologically active composite materials that are made of porous inorganic material and an infiltrant.

There is a need to provide methods for restoring an osseous void for situations requiring the use of a bone void filler for filling voids or gaps.

There is a need to provide methods to fill spaces between two bony structures to allow fusion, such as between the vertebral bodies of the spine.

There is a need to provide kits needed to create the biologically active composite, deliver the composite mass into a void, and therefore restore an osseous void.

SUMMARY OF THE INVENTION

This invention provides methods for preparing biologically active composite materials comprising aspirating or absorbing an infiltrant into at least one porous, biocompatible material; and maintaining the infiltrant and the porous material in contact under conditions effective to achieve at least partial coagulation of the infiltrant and porous material to form a self-supporting body. The porous, biocompatible material of the present invention can have pore volumes as low as 30%. Preferably, however, there exist other forms of this invention where the biocompatible material can have pore volumes of at least 70%, 85%, 88% or 90% to allow for proper infiltration of therapeutic materials. The biocompatible material can comprise synthetic bone mineral, ceramic material, calcium phosphate material, tri-calcium phosphate material or beta-tri-calcium phosphate. The porous material can be resorbable and at least one porous, biocompatible material is comprised of a resorbable beta-tri-calcium phosphate with interconnected micro-, meso- and macro-pores that render said at least one porous, biocompatible material at least 90% porous. The porous material can have pores with diameters down to less than 10 μm up to about 100 μm or greater. The aspirating or absorbing step can comprise aspirating therapeutic material onto the porous material or drawing bone marrow into a body of a syringe at least partially containing the porous material. The maintaining step can take place within a syringe or molded body to form a self-supporting body. The methods of the invention can further comprise manipulating the self-supporting body. The method can be further augmented by adding a composition such as a medicament to the self-supporting body or to the porous material. The infiltrants used in the present invention can be a variety of therapeutic materials.

In another aspect, the present invention provides methods for restoring osseous voids. Such methods comprise placing in the void at least a portion of a self-supporting body comprising partially coagulated infiltrant or therapeutic material in admixture with a porous, biocompatible material. The portion may be shaped to fit the void. Placement can be effected using a syringe, a tube, an insertion guide, a catheter or a shaped mold. The infiltrant can be bone marrow aspirate, replicated bone marrow or any therapeutic material.

The present invention also provides methods for restoring intraosseous voids comprising the steps of preparing the void, providing an aspirating means for holding porous, biocompatible material, aspirating bone marrow from an animal using the aspirating means or infiltrating the material with a therapeutic, so as to produce a biologically active composite of the aspirate/infiltrant and the porous material. The aspirate/infiltrant is allowed to at least partially coagulate, the composite is removed from the aspirating means and a portion of the composite is placed in the void. The aspirating means can be a syringe or other device capable of holding the composite and capable of acting as a delivery device. The composite can be shaped to fit said void prior to insertion into said void. The composite can be delivered into said void by syringe. The aspirate can be allowed to coagulate for a period of time and any remaining resultant composite can be preserved for later use. This preservation can be by freezing.

In yet another aspect, the present invention provides kits for the preparation and delivery of biologically active composites. In preferred embodiments, such kits comprise an instrument for the injection and the withdrawal of one or more fluids, as well as a porous, biocompatible material. The kits can also contain a plurality of syringes or pre-evacuated tubes. The biocompatible material can be in morsel or block form. The kits can also have a cutting instrument or spatula.

DETAILED DESCRIPTION OF PREFERRED EMBODIMENTS

Figure 1:
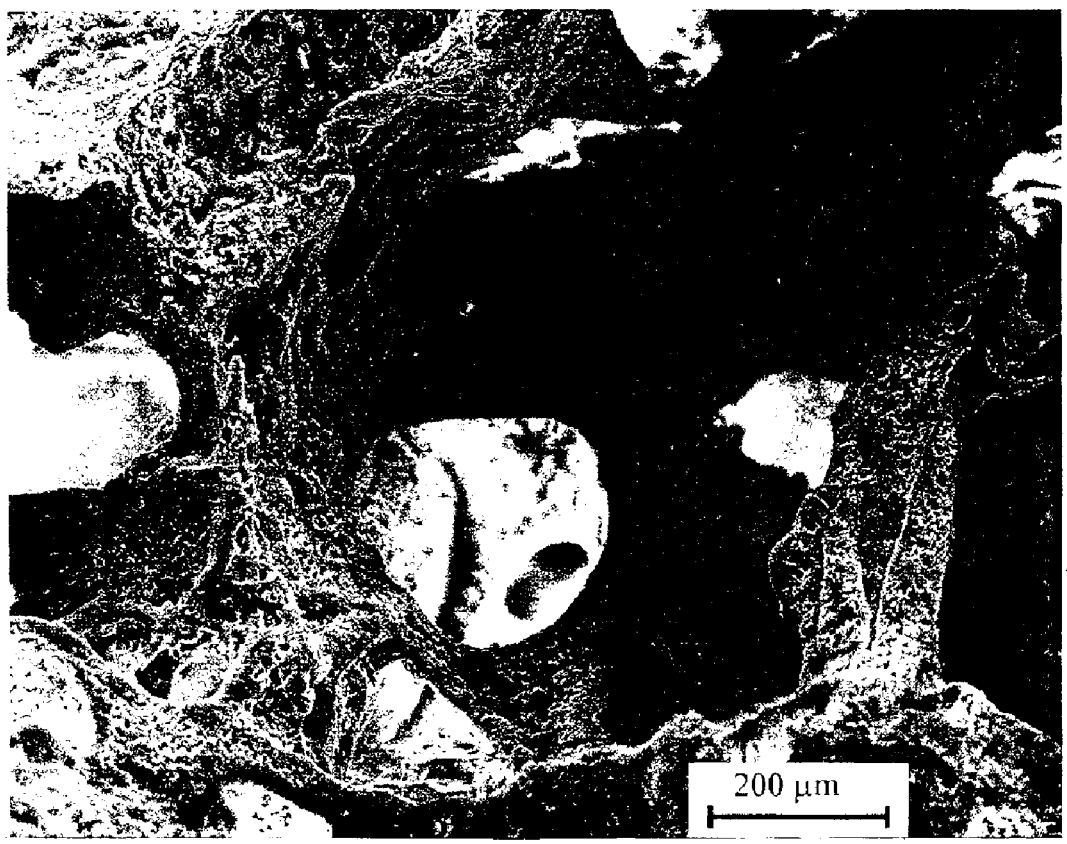
FIG. 1 is a scanning electron micrograph depicting the porosity of the porous calcium phosphate material of the present invention.

In accordance with the present invention, methods are provided for preparing biologically active composite materials comprising absorbing an infiltrant into at least one porous, biocompatible material; and maintaining the infiltrant and the porous material in contact under conditions effective to achieve at least partial coagulation of the infiltrant and porous material to form a self-supporting body. As used herein, therapeutic materials refer to one or more components of BMA including separated fractions of BMA, venous blood including one or more fractions of venous blood, concentrated platelets, thrombin, growth factors, growth hormones, proteins, genes, antibiotics, and cell signaling materials.

Representative porous biocompatible materials used in this invention include synthetic bone materials and ceramic materials, which can be made from a variety of calcium phosphate materials. Preferred porous, biocompatible bodies are those obtained generally in accordance with the disclosure of U.S. Pat. No. 5,939,039 filed Jan. 16, 1997, and issued Aug. 17, 1999; and U.S. application Ser. No. 09/253, 556 filed Feb. 19, 1999, now pending, assigned to the assignee of the present invention and incorporated herein by reference. Such bodies preferably exhibit interconnected macro-, meso- and microporosity throughout the bodies.

The infiltrants can be a number of substances that render the porous material bioactive. In many forms, the infiltrants can comprise therapeutic materials including growth factors or growth hormones that elicit bone formation and reparation. In other forms it may contain medicaments as one of its many ingredients. It may be preferred that the infiltrant contain one or more components of BMA. Bone marrow is a complex tissue comprised of cellular components that contribute to bone growth including red and white blood cells, their precursors and a connective tissue network termed the stroma. Bone marrow stromal cells or mesenchymal stem cells have the potential to differentiate into a variety of identifiable cell types including osteoblasts, fibroblasts, endothelial cells, reticulocytes, adipocytes, myoblasts and marrow stroma. Consequently, bone marrow aspirate is a good source of osteogenic cells for immediate transplantation. For subsequent use in transplantation, stem cells can also be cultured and expanded to many times their original number. Stromal cells regulate the differentiation of hemopoietic cells through cell-surface protein interactions and secretion of growth factors. Bone marrow has been successfully used to stimulate bone healing in many applications, suggesting a promptly renewable and reliable source of osteogenic cells without the disadvantages of open-grafting techniques. BMA also provides osteoinductive components, namely the progenitors of osteoblasts. Cell progenitors derived from bone marrow can be harvested by aspiration from patients, with limited dilution by peripheral blood if the volume of aspirate from a single site is held to 2 mL or less. Furthermore, the number of progenitors available in a graft site can be increased by concentration if necessary to further enhance the biologic result of bone grafting. Thus, the combination of a tri-calcium phosphate material as described herein with BMA yields a biologically active composite that is osteoconductive and, at least, osteoinductive or osteogenic. The biologically active composite is further rendered osteoinductive and osteogenic since the structure of the tri-calcium phosphate facilitates infusion of bone matrix proteins and growth factors. Osteogenic cells could also migrate into the open architecture of the scaffold and mingle with the seeded bone-forming cells, thereby enhancing the osteogenic properties of the β-TCP.

In embodiments that may be preferred by some in the art, bone reparation is accomplished by mixing porous bodies containing a polyporous material such as β-TCP material, with therapeutic material. The materials are allowed to coagulate to form a composite material having an improved handling consistency and osteogenic potential. In another embodiment, the polyporous material is mixed with BMA. Virtually any physical form of β-TCP material can be used, including morsels, blocks, etc. Subsequent to mixing with BMA, and packing in a desired conformation, BMA coagulates over time, thus binding the composite material together. In some embodiments that may be preferred, the coagulation can be for at least five minutes. The bound material behaves as a unit mass and can be surgically implanted by hand or with an instrument. The composite mass can be shaped by application of a gentle force, and/or by cutting. The composite mass can be packed into a bony void to create good contact with available bony surfaces.

Porous β-TCP synthetic cancellous bone void fillers that are low-density and highly porous resemble human cancellous bone in structure and composition. Generally, β-TCPs contain approximately 39% calcium and 20% phosphorus by weight and have the chemical formula $\beta\text{-}Ca_3(PO_4)_2$. By comparison, natural bone mineral is a carbonate-containing apatite that is approximately 35% calcium and 15% phosphorus. Hence, natural bone mineral and β-TCP are chemically similar. Used as a synthetic bone void filler, β-TCP can be engineered to fill voids or gaps. Blocks of β-TCP can be shaped with a scalpel before being placed into a defect. Additionally, morsels of β-TCP can be packed into an irregularly shaped defect site. When implanted in direct contact with viable host bone, β-TCP facilitates new bone ingrowth (osteoconduction) by serving as a scaffold upon which new bone deposits and matures. The scaffold is then removed by a combination of dissolution and phagocytosis (cell-mediated resorption).

It will be appreciated that preferred porous biocompatible materials according to the invention exhibit high degrees of porosity over a wide range of effective pore sizes. In this regard, such porous bodies preferably have, at once, macroporosity, mesoporosity and microporosity as depicted in FIG. 1. Macroporosity is characterized by pore diameters greater than about 100 μm. Mesoporosity is characterized by pore diameters between about 100 and 10 μm, while microporosity occurs when pores have diameters below about 10 μm. It is preferred that macro-, meso- and microporosity simultaneously occur in a random and interconnected nature throughout the porous material used in the invention. It is not necessary to quantify each type of porosity to a high degree. Rather, persons skilled in the art can easily determine whether a material has each type of porosity through examination, such as through methods of scanning electron microscopy or mercury porosimetry.

In some embodiments that may be preferred, the porous materials can have pore volumes of at least about 30%. In other typical embodiments, the porous materials can have pore volumes of at least about 70%, more preferably in excess of about 85%, with 90% being still more preferred. In preferred cases, such high pore volumes are attained while also attaining the presence of macro-, meso- and micro-porosity as well as physical stability of the materials produced. In one typical embodiment of the invention, the porous biocompatible material is an osteoconductive tri-calcium phosphate material with interconnected micro, meso and macro-pores, which, together, impart a pore volume of at least 90% to the porous material. It is believed to be a great advantage to be able to prepare inorganic shaped bodies having interconnected macro-, meso- and micro-porosity with high pore volumes to permit more thorough infiltration of therapeutics, a more continuous supply of nutrients, more extensive cellular and tissue ingrowth into the scaffold, and enhanced revascularization, allowing bone growth and repair to take place more efficiently.

The present invention has utility in a wide variety of applications. The porous shaped bodies can be used in medicine, for example, for the restoration of bony defects and the like. The materials can also be used for the delivery of healing materials, such as medicaments, internal to the body. When used with medicaments, the porosity of a material formed in accordance with the invention can be all or partially filled with another material, which either comprises or carries the medicaments. Indeed, the larger porous spaces within some of the products of the present invention can be used for the culturing of cells within the human body. In this regard, the larger spaces are amenable to the growth of cells and can be permeated readily by bone cells and bodily fluids such as certain blood components. Growing cells can also be implanted in an animal through the aegis of implants in accordance with the present invention. The implants described herein can give rise to important biochemical or therapeutic or other uses.

The methods of the present invention can further include an absorbing step comprising aspirating therapeutic material onto the porous material. The aspirating step can comprises drawing bone marrow into a body of a syringe at least partially containing the porous material. The maintaining step, which can takes place within a syringe, further comprises extruding the self-supporting body. Some skilled in the art may choose to manipulate the self-supporting body as part of one of the methods disclosed. Many methods can further comprise adding a healing composition, such as a medicament, to the self-supporting body or to the porous material. In other methods, the infiltrant can consist of bone marrow aspirate.

Figure 2A:
FIGS. 2A and 2B illustrate one embodiment of the porous, biocompatible material of the present invention shaped into a block form and used in a tibial plateau reconstruction that is screwed, bonded, cemented, pinned, anchored, or otherwise attached in place.
Figure 2B:
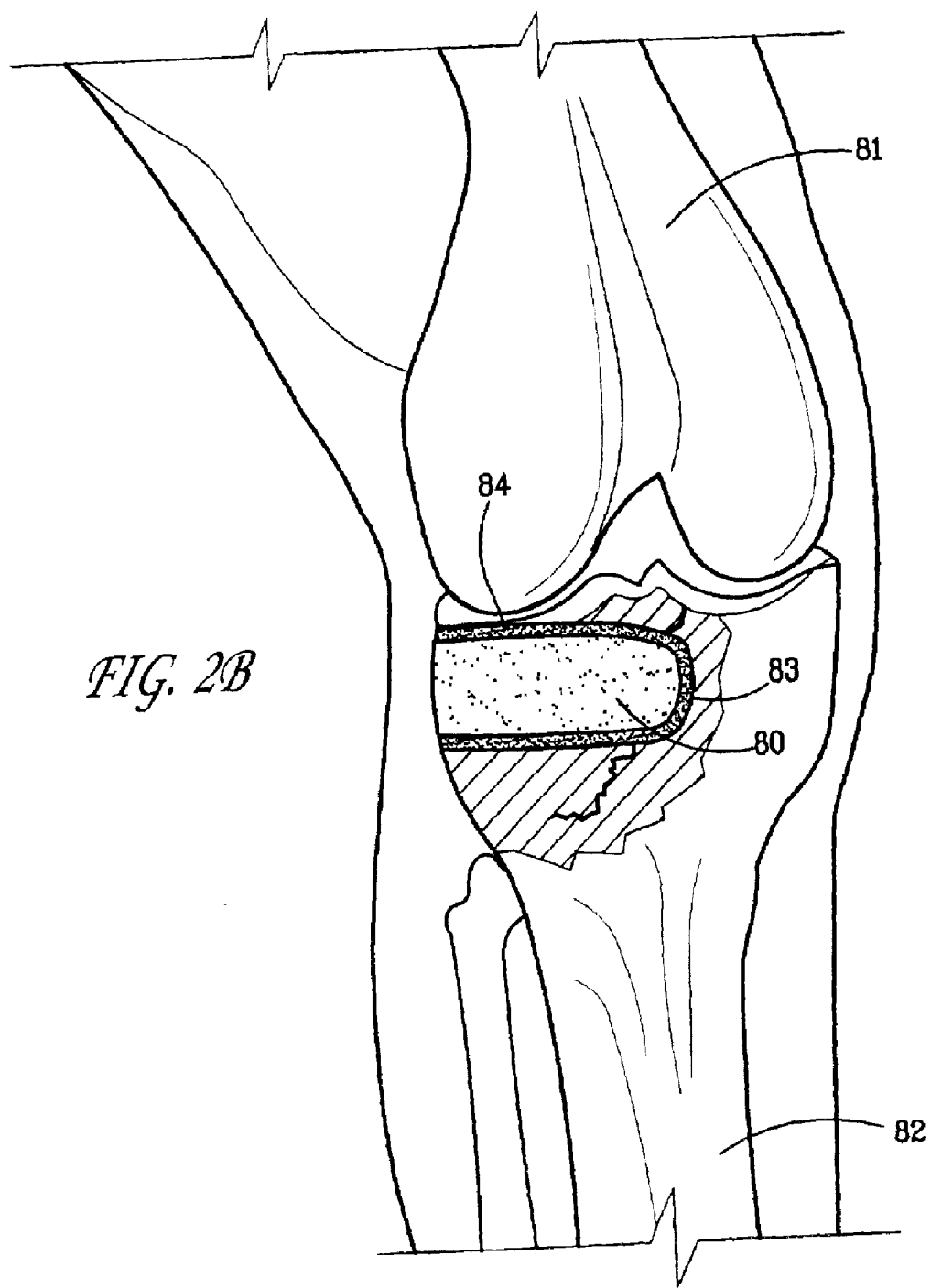

FIG. 2A depicts a plug of the porous, calcium phosphate scaffolding material 80. FIG. 2B illustrates plug 80, which is inserted into an excavation site 83 within a human knee, below the femur 81 and above the tibia 82, for use in a tibial plateau reconstruction. Plug 80 is held in place or stabilized via a bone cement layer 84. In the present invention, plug 80 is imbibed with an infiltrant prior to insertion for reparation, as disclosed herein.

Figure 3:
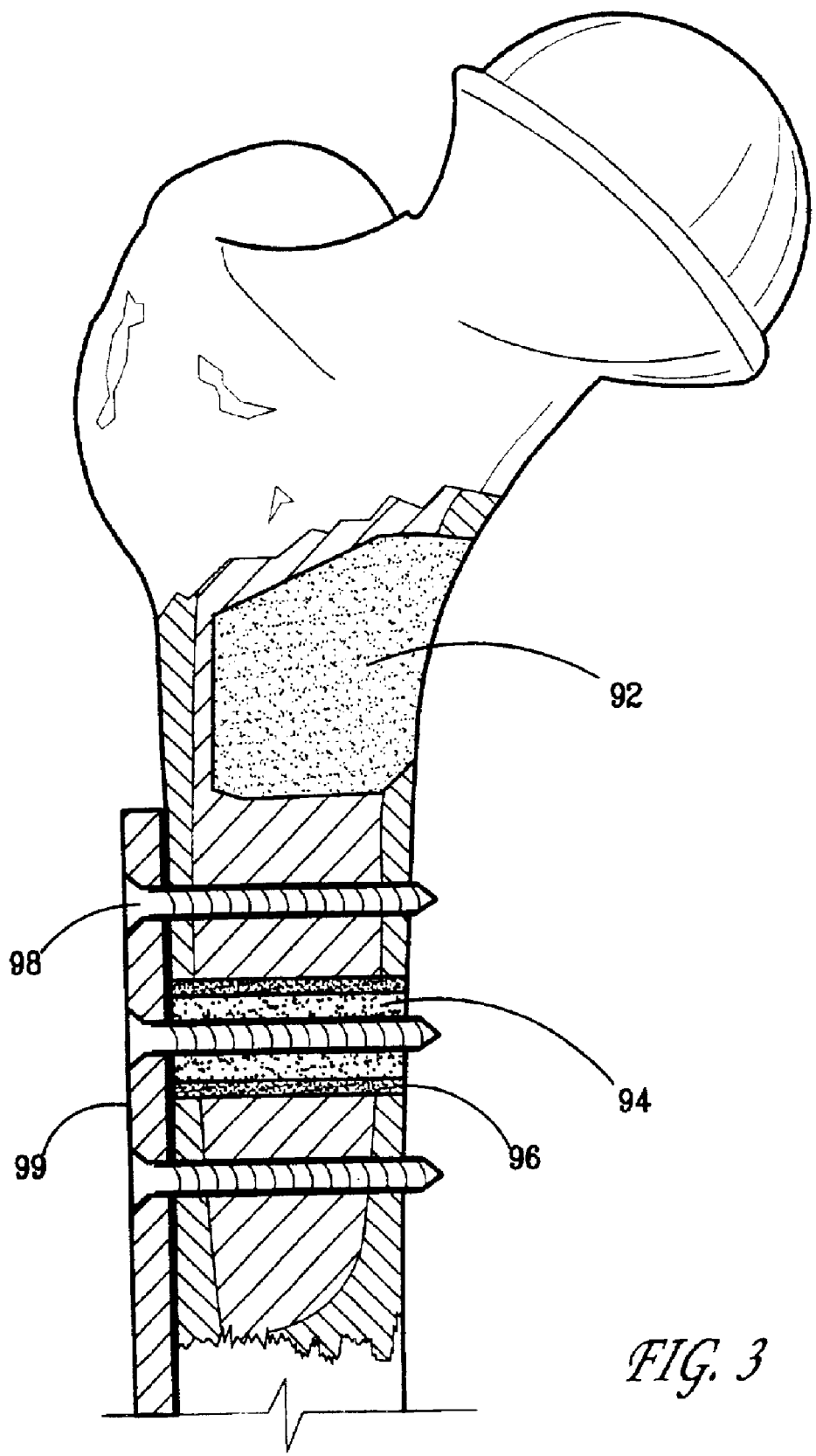
FIG. 3 illustrates an embodiment of the porous calcium phosphate scaffolding material preferred in the present invention shaped into a block or sleeve form and used for the repair or replacement of bulk defects in metaphyseal bone, oncology defects or screw augmentation.

FIG. 3 shows the calcium phosphate scaffolding material within a human femur that is used as a block 92 for bulk restoration or repair of bulk defects in metaphyseal bone or oncology defects, or as a sleeve 94 for an orthopaedic screw, rod or pin 98 augmentation. Item 99 depicts an orthopaedic plate anchored by the orthopaedic device item 98. Bone cement layer 96 surrounds and supports sleeve 94 in place. In the present invention, a block 92 is imbibed with an infiltrant prior to insertion for reparation, as disclosed herein.

In accordance with this invention, methods are provided for restoring an osseous void comprising placing in said void at least a portion of a self-supporting body comprising partially coagulated infiltrant in admixture with a porous, biocompatible material. In one embodiment that may be preferred, the composites used to fill the void are comprised of a porous biocompatible material imbibed throughout its structure with an infiltrant or therapeutic material for a predetermined period of coagulation. The resultant composite is sufficiently self-supporting to be handled with surgical hand tools such as spatulas and knives. The composite need not be entirely stiff but can tend to flow under force. Typically, a shapeable portion of the composite can be placed into a bone void. The shaping of the composite can take place before placing it into the osseous void or performed while in the void. Any remaining composite can be preserved in a freezer or other suitable means of preserving.

The placement of the self-supporting body can be effected using a syringe. In many other embodiments the placement may be effected using a tube, insertion guide, catheter or shaped mold.

The tri-calcium phosphate in the many embodiments of the present invention is resorbable. Resorption of calcium-based bone implants is influenced largely by the composition, physical structure and solubility of the implant. The porous bodies that may be preferred in some embodiments of the present invention have significant resorption due to their low density, high porosity, nano-size particle composition, and chemistry. As calcium-based implants are resorbed, they are often replaced by new bone. Porous tri-calcium phosphate bone implants can resorb more quickly than porous hydroxyapatite. The porous tri-calcium phosphate resorption rate is concurrent with the rapid rate of ingrowth and remodeling of new bone.

The present invention can call for the use of therapeutic materials or any mixture of materials therein, as an alternative to BMA or in conjunction therewith. Replicated bone marrow or other types of bioengineered bone marrow material can be used in this invention. Exemplary therapeutic materials include signaling molecules under the Transforming Growth Factor (TGF) Superfamily of proteins, specifically proteins under the TGF-beta (TGF-β), Osteogenic Protein (OP)/Bone Morphogenic Protein (BMP), VEGF (VEGF-1 and VEGF-2 proteins) and Inhibin/activtin (Inhibin-beta A, Inhibin-beta B, Inhibin-alpha, and MIS proteins) subfamilies. Most preferably, the exemplary therapeutic materials are proteins under the TGF-β and OP/BMP subfamilies. The TGF-β subfamily includes the proteins Beta-2, Beta-3, Beta-4 (chicken), Beta-1, Beta-5 (xenopus) and HIF-1 alpha. The OP/BMP subfamily includes the proteins BMP-2, BMP-4, DPP, BMP-5, Vgr-1, OP-1/BMP-7, Drosophila 60A, GDF-1, Xenopus Vg-1 and BMP-3. Representative proteins of these types include: OP-1/rhBMP-7 (Stryker Corporation, Kalamazoo, Mich.), rhBMP-2 (Genetics Institute/American Home Products, Madison, N.J.), IGF-1 (Insulin-like Growth Factor-1) (Cephalon, West Chester, Pa.), TGF beta (Genentech, San Francisco, Calif.), MP52 (Biopharm GmbH, Heidelberg, Germany). Other proteins, genes and cells outside the TGF Superfamily may also be included in the exemplary types of therapeutic materials to be used in conjunction with the present invention. These other proteins, genes and cells include PepGen P-15 (Ceramed, Lakewood, Colo.), LMP-1 (LIM Mineralized Protein-1 gene) (Emory University, Atlanta, GA/Medtronic Sofamor Danek, Minneapolis, Minn.), Chrysalin TP 508 Synthetic Peptide (Chrysalis Biotechnology, Galveston, Tex.), GAM (parathyroid hormone) (Selective Genetics, San Diego, Calif.), rhGDF-5 (Orquest, Mountain View, Calif.), cell lines and FGF (Fibroblast Growth Factor) such as BFGF (Basic Fibroblast Growth Factor), FGF-A (Fibroblast Growth Factor Acidic), FGFR (Fibroblast Growth Factor Receptor) and certain cell lines such as osteosarcoma cell lines. The therapeutic materials to be used with the present invention material may also be combinations of those listed above. Such mixtures include products like Ne-Osteo GFm (growth factor mixture) (Sulzer Orthopaedics, Austin, Tex.), or mixtures of growth factors/proteins/genes/cells produced by devices such as AGF (Autologous Growth Factor) (Interpore Cross International, Irvine, Calif.), Symphony Platelet Concentrate System (Harvest Technologies, Belton, TX/DePuy, Warsaw, Ind.), and the like.

According to the present invention, there are methods for restoring an intraosseous void comprising preparing said void; providing an aspirating means having porous material therein; aspirating bone marrow from an animal using the aspirating means; allowing BMA to mix with the porous material, thereby producing a composite of said aspirate and said porous material; allowing said aspirate to at least partially coagulate; removing the said composite from the aspirating means; and placing at least a portion of said composite into said void.

A syringe can be used as an aspirating means for the porous materials. Also well suited as an aspirating means is a shaped mold, catheter tube, insertion guide or the like. The resultant composites of the present invention can be saved for later use. They can also be preserved by a variety of methods known in the art including freezing.

Figure 4:
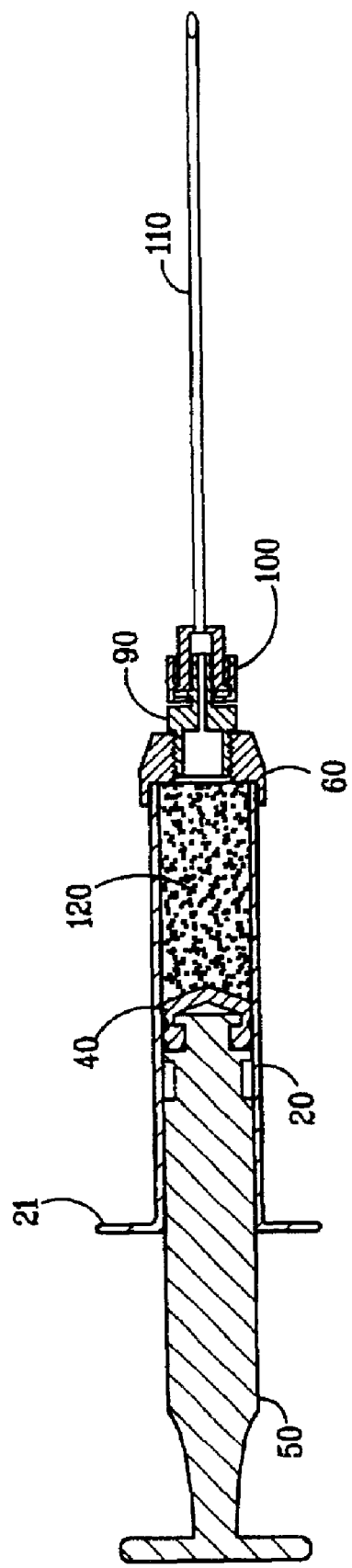
FIG. 4 depicts a syringe device for use in infiltrating and delivering the present invention composite.

The methods of the present invention give rise to kits that are unique in their ability to prepare and deliver the biologically active composite. A preferred embodiment is made of a syringe capable of holding porous, biocompatible material. The syringe is used to prepare the composite when a therapeutic such as BMA is absorbed into the porous material by the aspiration process. A typical syringe device is shown in FIG. 4. The composite is formed within the barrel 20 of the syringe once the aspirate coagulates with the porous material 120. The syringe used can be of varying volumes, shapes and cross sections. The same syringe can be used to deliver the resultant composite by removing the end portion and extruding the composite to be placed into an osseous void.

It will be appreciated that a number of surgical devices can be used to aspirate bone marrow. In other embodiments a shaped mold, catheter tube, insertion guide and the like can be used to aspirate. Coagulation also need not take place in the body of any of these devices but may be transferred to another container. The composite can then be removed and sculpted using a scalpel or other instrument before placement into a void. The composite can already be formed by virtue of the shape of the container chosen.

As will be appreciated, other forms of surgical devices can be used in addition to a syringe, and each device can be housed as part of a kit. In this manner, a number of syringes can be included in the kit. In one embodiment of the present invention a small 1 cc syringe is used to aspirate the bone marrow and to deliver the aspirate into a second syringe, container or mold holding the porous material. Some kits can also include a pre-evacuated tube to aspirate bone marrow. Other kits can be expanded further by including cutting instruments, such as a scalpel or knife, and other surgical hand tools used to shape and mold the composite, such as a spatula.

Additional objects, advantages, and novel features of this invention will become apparent to those skilled in the art upon examination of the following examples thereof, which are not intended to be limiting.

EXAMPLES

Example 1

Healing of Tibial Segmental Defects in Dogs Using Biologically Active Composites Thirty-five vials of a porous, biocompatible material such as VITOSS™ Scaffold Synthetic Cancellous Bone Void Filler morsels (provided by Orthovita of Malvern, Pa.), referred to herein as "Test Article", were prepared and assigned a unique identification number for the study. Table I provides the animal subjects' ID number, test article ID numbers, amount of biological material imbibed into the VITOSS porous scaffold material, and the amount in grams of residual VITOSS and BMA composite.

| Animal ID | Test Article ID | Amount Mixed (g) | Residual VITOSS ™/BMA (cc) |
| --- | --- | --- | --- |
| 11A | ORL-131-T | 0.72 | 0.9 |
| 11B | ORL-101-T | 0.54 | 0.3 |
| 11C | ORL-117-T | 0.72 | 1.0 |
| 11D | ORL-131-T | 0.80 | 0.7 |
| 11E | ORL-109-T | 0.37 | 0.4 |
| 12A | ORL-134-T | 0.79 | N/A |
| 12B | ORL-119-T | 1.04 | N/A |
| 12C | ORL-101-T | 1.21 | N/A |
| 12D | ORL-109-T | 0.45 | N/A |
| 12E | ORL-127-T | 1.15* | 3.0* |
| 13A | ORL-113-T | 0.76 | 0.2 |
| 13B | ORL-113-T | 0.85 | 0.3 |
| 13C | ORL-119-T | 0.77 | N/A |
| 13D | ORL-118-T | 0.94 | 0.3 |
| 13E | ORL-131-T | 0.88 | 0.6 |
| 14A | ORL-134-T | 0.86 | 0.3 |
| 14B | ORL-118-T | 1.61* | N/A* |
| 14C | ORL-100-T | 0.93 | N/A |
| 14D | ORL-133-T | 0.79 | N/A |
| 14E | ORL-133-T | 0.97 | N/A |
| 15A | ORL-113-T | 0.79 | N/A |
| 15B | ORL-134-T | 0.83 | 0.4 |
| 15C | ORL-133-T | 0.75 | 0.1 |
| 15D | ORL-131-T | 0.84 | 0.5 |
| 15E | ORL-109-T | 0.74 | N/A |
| 16A | ORL-134-T | 0.73 | N/A |
| 16B | ORL-119-T | 0.81 | N/A |
| 16C | ORL-117-T | 0.75 | N/A |
| 16D | ORL-117-T | 1.05 | N/A |
| 16E | ORL-127-T | 0.90 | N/A |

*An additional quantity of VITOSS/BMA was prepared for use if necessary.

Surgical procedures were scheduled in "sessions", with three surgical procedures typically performed per session. Prior to the start of each surgery session, a vial of Test Article was removed from the sterile packaging for use during the entire session. Care was taken to maintain sterility of the vial throughout the session.

While maintaining sterility, each vial of Test Article was weighed prior to and following removal of material for placement in each Test System. The total amount of Test Article used in each Test System was determined in this way.

Prior to the first surgical procedure, the method for preparing and mixing the Test Article was determined in detail. The method, as described in Protocol Amendment 4, is as follows:

1. A 5 cc syringe was filled to the 4 cc mark with Test Article.
2. The syringe was tapped to settle the Test Article.
3. The syringe plunger was then compressed to the 3 cc mark.
4. The syringe containing the Test Article was attached to the needle being used for BMA collection.
5. BMA was either: (1) drawn into the syringe through the Test Article such that it completely saturated it; or (2) drawn into a 1 cc syringe and then transferred to the 5 cc syringe containing the VITOSS™ scaffold material such that the BMA completely saturated it. In some cases, the syringe was removed to withdraw air and reattached.
6. Following saturation, the plunger was compressed to the 3 cc mark.
7. The syringe containing the mixture was allowed to sit for at least 5 minutes.
8. The tip was removed from the syringe so that the mixture could be removed.
9. The mixture was placed into the defect and finger packed.

Thirty animals underwent an identical surgical procedure. Surgery was performed in accordance with the following study protocol. The experimental hind limb was prepped and draped in standard sterile fashion. The lilac crest was exposed laterally through a 2 cm or smaller skin incision and BMA was collected using a 13 or 15 gauge Jamshidi needle and syringe. The BMA was then mixed with the VITOSS to provide a biological composite. At least 3 cc of BMA was collected from the animal for mixing. The amount of VITOSS scaffold material that was mixed with the BMA is provided in Table I.

Following closure of the marrow harvest site, a four-pin, Type 1 Kirschner external fixator was placed on the anterio-lateral aspect of the experimental tibia. A medial skin incision approximately 3 cm in length was made and exposure of the tibia was obtained using sharp and blunt dissection. Once exposed, the periosteum was scored and reflected back. The major axis of the mid-section of the tibia was then measured. A cortical segmental defect approximately two times the mid-shaft major axis dimension was created in the mid-tibia using an oscillating saw. The defect was then completely filled with VITOSS™ and the periosteum closed with non-absorbable suture to contain it. The residual amount of remaining biological composite after the defect was filled is shown in Table I. The soft tissues were closed in layers.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for restoring an intraosseous void comprising:
   preparing said void;
   providing an aspirating means having porous, biocompatible material having macro-, meso-, and microporosity therein;
   aspirating bone marrow from an animal using said aspirating means;
   saturating said porous material with said bone marrow aspirate;
   allowing said aspirate to at least partially coagulate;
   removing said composite from the aspirating means; and
   placing at least a portion of said composite into said void.

2. The method of claim 1 wherein said composite is shaped to fit said void prior to insertion into said void.

3. The method of claim 1 wherein said aspirating means is a syringe.

4. The method of claim 3 wherein resultant composite is delivered into said void by syringe.

5. The method of claim 1 wherein the aspirate is allowed to coagulate for at least five minutes.

6. The method of claim 1 further comprising preserving any remaining resultant composite for later use.

7. The method of claim 1 wherein preservation is by freezing.

8. The method of claim 1 wherein the porous material is comprised of a resorbable beta-tri-calcium phosphate with interconnected micro, meso and macro pores that render said porous biocompatible material at least about 90% porous.

* * * * *